United States Patent [19]

Appling

[11] Patent Number: 5,034,005
[45] Date of Patent: Jul. 23, 1991

[54] RADIOPAQUE MARKER

[76] Inventor: William M. Appling, RD2, Box 2109, Hartford, N.Y. 12838

[21] Appl. No.: 549,959

[22] Filed: Jul. 9, 1990

[51] Int. Cl.⁵ .......................................... A61M 25/00
[52] U.S. Cl. ..................................... 604/280; 128/658
[58] Field of Search ..................... 604/280, 265, 283; 128/657, 658

[56] References Cited

U.S. PATENT DOCUMENTS

| | | | |
|---|---|---|---|
| 3,399,668 | 9/1968 | Lundgren | 604/280 X |
| 3,605,750 | 9/1971 | Sheridan et al. | 128/658 |
| 4,279,252 | 7/1981 | Martin | 604/280 |
| 4,430,083 | 2/1984 | Ganz et al. | 604/265 |
| 4,938,220 | 7/1990 | Mueller, Jr. | 128/658 |

Primary Examiner—John D. Yasko
Attorney, Agent, or Firm—McAulay Fisher Nissen Goldberg & Kiel

[57] ABSTRACT

A radiopaque marker usable with catheters is provided. The marker is shaped and dimensioned to fit within a catheter lumen. The marker has an annular sidewall which defines a marker lumen. The marker has a proximal end and a distal end. It further includes securing barbs to prevent the marker from exiting from the catheter lumen.

15 Claims, 1 Drawing Sheet

RADIOPAQUE MARKER

BACKGROUND OF THE INVENTION

Radiopaque Markers are used with catheters to enable the catheter to be visualized during x-ray and fluoroscopic procedures.

Known radiopaque markers used with catheters are attached to the outer wall of the catheter. Although these markers allow the catheter to be visualized they can create certain problems. Placing a radiopaque marker on the outer wall of the catheter adversely effects wall smoothness and this can cause damage to the blood vessels into which the catheter is introduced. Further, the placement of radiopaque markers on the outer catheter wall presents problems with inadvertent disassociation of the marker from the catheter wall with attendant medical complications.

Accordingly, it is an object of the present invention to provide a radiopaque marker for use with a catheter which does not impact upon the smoothness of the outer catheter wall.

It is a further object of the present invention to provide such a marker which securely connects to the catheter to prevent inadvertent separation therefrom.

BRIEF DESCRIPTION

In one embodiment of the present invention a radiopaque marker for use with catheters is provided. The radiopaque marker has an outer annular sidewall which defines a marker lumen. The marker is shaped and dimensioned to securely fit within the lumen of the catheter. The marker is provided with securing portions to prevent the marker from being dislodged from the catheter lumen.

DESCRIPTION OF THE PREFERRED EMBODIMENT

Figure 1:
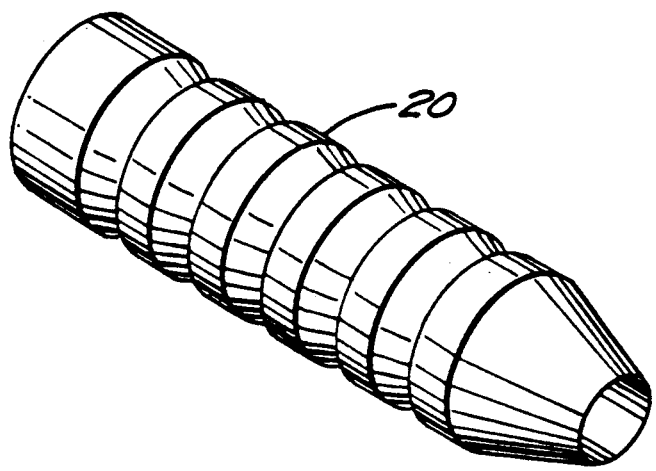
FIG. 1 is a perspective view of the marker of the present invention.
Figure 2:
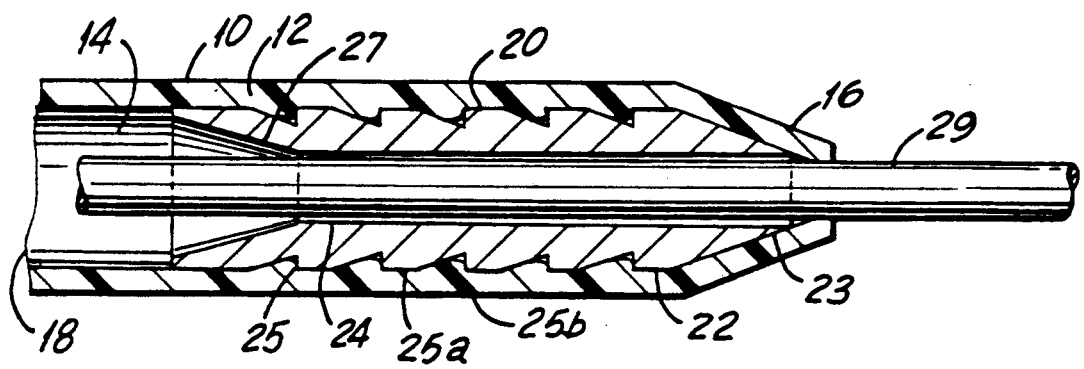
FIG. 2 is a sectional view showing the FIG. 1 marker in place in a catheter lumen.

Referring now to the drawings the reference numeral 10 generally denotes a catheter for use in the vascular system. Catheter 10 has an annular side wall 12 defining a catheter lumen 14. In a preferred embodiment of the invention catheter 10 is narrower at its distal end 16 than at its proximal end 18.

Catheter 10 has an associated radiopaque marker 20. Radiopaque marker 20, as shown in the drawings, sits within the catheter lumen 14 proximate to the distal end 16 thereof. In the preferred embodiment of the invention radiopaque marker 20 is formed of surgical grade stainless steel.

Radiopaque marker 20 has an annular sidewall 22 which defines a marker lumen 24. The annular sidewall 22 tapers at its distal end 23. The outer diameter of distal end 23 is formed to provide a close fit within the narrowed lumen of the catheter distal end 16.

In one embodiment of the invention radiopaque marker 20 is used in a four French catheter having an inner diameter of about 0.038 inches. In this embodiment the outer diameter of radiopaque marker 20 is about 0.039 inches. In another embodiment of the invention radiopaque marker 20 is used in a five French catheter having an inner diameter of about 0.048 inches. In this embodiment the outer diameter of radiopaque marker 20 is about 0.050 inches. In both embodiments radiopaque marker 20 is inserted into the catheter as follows: The catheter, which is generally made of nylon, is heated enough to swell. The radiopaque marker is then inserted into the catheter lumen 14 and when the catheter cools, the annular sidewall 12 shrinks around the radiopaque marker 20. Because of the relative dimensions of marker 20 and catheter lumen 12 and because the catheter tapers at its distal end 16, once the marker is inserted into the catheter lumen it cannot move outwardly through the distal end of the catheter.

To prevent marker 20 from moving outwardly from the proximal end of the catheter, the marker 20 is formed with a plurality of sharp-edged barbs 25. In the preferred embodiment of the invention there are five barbs 25 formed on the sidewall 22 of radiopaque marker 20. Barbs 25 are shaped to prevent the radiopaque marker 20 from moving out from the proximal end of the catheter. Each barb 25 have a flat edge 25a and an angled edge 25b. Generally each flat edge 25a is about 0.010 inches in length and each angled edge 25b is about 0.015 inches in length. When the radiopaque marker 20 is formed for use with a four French catheter the groove of the barb 25 has a depth of about 0.003 inches. When marker 20 is formed for use with a five French catheter the groove of the barb 25 has a depth of about 0.005 inches.

In a preferred embodiment of the invention the radiopaque marker 20 has a length of about 0.2 inches. About 0.04 inches of the marker length comprises the narrow distal end 23. The distal end of the radiopaque marker 20 is formed to have a radius of sufficient size to prevent puncturing the catheter sidewall. In the preferred embodiment of the invention the radius of the distal end of the radiopaque marker is about 0.0025 inches.

Marker lumen 24 is shaped and dimensioned to allow a guide wire to fit therethrough. The inner diameter of the lumen 24, in a preferred embodiment of the invention, is about 0.023 inches. To further enable the guide wire to fit within the radiopaque marker 20 the proximal interior surface 27 of the marker is formed with a truncated conical zone 27 which in the preferred embodiment is at an angle of about 15 degrees to the central marker axis. This truncated zone 27 acts as a guide means for guiding a guide wire 29 into marker lumen 24 by avoiding the presence of a shoulder which could impede the introduction of the guide wire into the marker lumen 24.

The shape of the barb 25 allow the radiopaque marker to be introduced into the catheter lumen but prevent the marker from backing out from the proximal catheter end.

I claim:

1. A radiopaque marker for use with catheters the marker comprising:

a marker body shaped and dimensioned to fit within a catheter having a narrow distal end, the marker body having a side wall defining a marker lumen, the marker body having a proximal end and a distal end, the distal end of the marker being narrower than its proximal end; and securing means associated with said marker body to prevent the marker from exiting from the catheter lumen.

2. A radiopaque marker for use with catheters the marker comprising:
   a marker body shaped and dimensioned to fit within a catheter lumen, the marker body having a side wall defining a marker lumen, the marker having a proximal end and a distal end; and
   a plurality of barbs formed on the marker side wall, the barbs capable of securing the marker to the catheter lumen.

3. The marker of claim 1 wherein said securing means includes a plurality of barbs formed on the marker sidewall, the barbs capable of securing the marker to the catheter lumen, the barbs together with the relative shapes and dimensions of the catheter lumen and marker holding hold the marker in the catheter lumen.

4. The marker of claim 1 or 2 wherein said marker is formed of stainless steel.

5. The marker of claim 1 or 2 wherein said marker is about 0.2 inches in length.

6. The marker of claim 1 or 2 wherein the proximal end of the marker has an outer diameter of about 0.039 inches and wherein the marker is used with a catheter having an inner diameter of about 0.038 inches.

7. The marker of claim 1 or 2 wherein the proximal end of the marker has an outer diameter of about 0.050 inches, and wherein the marker is used with a catheter having an inner diameter of about 0.047 inches.

8. The marker on claim 3 wherein the proximal end of the marker has an outer diameter of about 0.039 and wherein the marker is used with a catheter having an inner diameter of about 0.038 inches.

9. The marker of claim 3 wherein the proximal end of the marker has an outer diameter of about 0.050 inches, and wherein the marker is used with a catheter having an inner diameter of about 0.047 inches.

10. The marker of claim 1 or 2 wherein said marker lumen has an inner diameter of about 0.023 inches.

11. The marker of claim 2 wherein each barb is comprised of a flat edge having a length of about 0.010 inches and an angled edge having a length of about 0.015 inches.

12. The marker of claim 2 wherein each barb has a groove.

13. The marker of claim 2 wherein the grooves have a depth of about 0.003 to 0.005 inches.

14. The marker of claim 1 or 2 wherein the marker includes guide means of guiding a guidewire into the marker lumen.

15. The marker of claim 14 wherein the guide means is a truncated conical zone on the proximal interior surface of the marker.

* * * * *

UNITED STATES PATENT AND TRADEMARK OFFICE
CERTIFICATE OF CORRECTION

PATENT NO.  :  5,034,005
DATED       :  July 23, 1991
INVENTOR(S) :  William M. Appling It is certified that error appears in the above-identified patent and that said Letters Patent is hereby corrected as shown below:

On the cover page, after the Inventor block, the following block should appear:

[73] Assignee: E-Z-EM, Inc., Westbury, N.Y.

Signed and Sealed this

Twenty-ninth Day of December, 1992

Attest:

DOUGLAS B. COMER

*Attesting Officer*     Acting Commissioner of Patents and Trademarks